United States Patent [19]

Mehra

[11] Patent Number: 5,439,484
[45] Date of Patent: Aug. 8, 1995

[54] DEFIBRILLATOR EMPLOYING TRANSVENOUS AND SUBCUTANEOUS ELECTRODES

[75] Inventor: Rahul Mehra, Stillwater, Minn.

[73] Assignee: Medtronic, Inc., Minneapolis, Minn.

[21] Appl. No.: 230,962

[22] Filed: Apr. 21, 1994

[51] Int. Cl.⁶ .................................... A61N 1/39
[52] U.S. Cl. .......................... 607/5; 607/129
[58] Field of Search .................... 607/129, 5, 152

[56] References Cited

U.S. PATENT DOCUMENTS

| Re. 27,652 | 9/1973 | Mirowski et al. |
|---|---|---|
| 4,161,952 | 7/1979 | Kinney et al. |
| 4,481,953 | 11/1984 | Gold et al. |
| 4,641,656 | 2/1987 | Smits |
| 4,708,145 | 11/1987 | Tacker et al. |
| 4,727,877 | 3/1988 | Kallok |
| 4,765,341 | 8/1988 | Mower et al. |
| 4,817,634 | 4/1989 | Holleman et al. |
| 4,834,100 | 5/1989 | Charms |
| 4,922,927 | 5/1990 | Fine et al. |
| 4,934,049 | 6/1990 | Kiekhafer et al. |
| 4,953,551 | 9/1990 | Mehra et al. |
| 5,042,143 | 8/1991 | Holleman et al. |
| 5,044,374 | 9/1991 | Lindemans |
| 5,099,838 | 3/1992 | Bardy |
| 5,133,353 | 7/1992 | Hauser |
| 5,261,400 | 11/1993 | Bardy |

FOREIGN PATENT DOCUMENTS 0453761 3/1991 European Pat. Off.

*Primary Examiner*—William E. Kamm
*Assistant Examiner*—Scott M. Getzow
*Attorney, Agent, or Firm*—Reed A. Duthler; Harold R. Patton

[57] ABSTRACT

A defibrillation pulse generator and lead system particularly adapted to allow for implant in a single incision and subcutaneous pocket. The electrode system consists of a right ventricular electrode and a combined, subcutaneously implanted pulse generator housing and flexible periprerally extending electrode. The flexible electrode extends in a generally co-planar relation with respect to the major surfaces of the device housing and may comprise a plurality of electrode segments electrically connected in common with the device housing and distributed over a flexible electrode pad.

7 Claims, 3 Drawing Sheets

DEFIBRILLATOR EMPLOYING TRANSVENOUS AND SUBCUTANEOUS ELECTRODES

BACKGROUND OF THE INVENTION

The present invention relates to medical electrodes and leads generally, and more particularly to implantable defibrillation electrodes and leads.

By way of definition, in the field of automatic implantable arrhythmia control devices, the term "cardioversion" or "cardioverter" refers to the process of and device for discharging relatively high energy electrical pulses into or across cardiac tissue to arrest a life threatening tachyarrhythmia. Cardioversion pulses may or may not be synchronized with a cardiac depolarization or rhythm and may be applied to arrest a ventricular tachycardia with a lower range energy pulse or ventricular fibrillation with a medium to high energy pulse. The arrest of ventricular fibrillation by such pulses is referred to as "defibrillation", a form of cardioversion, and "defibrillators" have been characterized as a form of cardioverter. In the following description and claims, it is to be assumed that these terms are interchangeable, and that use of one term is inclusive of the other device or operation, unless specific distinctions are drawn between them in the context of the use.

Early concepts of implantable defibrillators, such as disclosed in U.S. Pat. No. Re. 27,652 by Mirowski et al., envisioned an electrode system employing a ventricular endocardial electrode and a plate electrode mounted to the heart or implanted subcutaneously. However, early commercially available implantable defibrillators typically employed multiple epicardial electrodes, the surgical implantation of which required a thoracotomy.

More recent implantable defibrillators employ systems of endocardial and optionally subcutaneous electrodes which avoid the necessity of a thoracotomy. Electrode systems of this type are disclosed in U.S. Pat. No. 4,727,877 issued to Kallok, U.S. Pat. No. 4,708,145 issued to Tacker et al., U.S. Pat. No. 4,922,927, issued to Fine et al., U.S. Pat. No. 5,261,400 issued to Bardy and U.S. Pat. No. 5,099,838 issued to Bardy, all incorporated herein by reference in their entireties.

The subcutaneous leads employed in the systems as discussed above may be fabricated using metal mesh electrodes, as disclosed in U.S. Pat. No. 4,765,341, issued to Mower et al, or coiled metal wire electrodes as disclosed in commonly assigned U.S. Pat. Nos. 4,817,634, issued to Holleman et al., and 5,044,374, issued to Lindemans, or may be the external surface of the metal enclosure of the defibrillator pulse generator as disclosed in the above-cited Kallok, Bardy '400 and Fine patents.

In U.S. Pat. No. 5,133,353, issued to Hauser, a "mesh" electrode formed on a portion of the pulse generator case is employed as one electrode in a two or three electrode system. It is suggested that a further conductive patch electrode may be attached by means of an attachment mechanism to the pulse generator housing to increase the conductive surface area.

Further efforts to enhance efficacy and decrease cardioversion/defibrillation efficiency have led to the suggestion of a wide variety of pulse wave forms and polarities for use as cardioversion/defibrillation shock pulses. Monophasic capacitive discharge pulses are disclosed in the above cited Mirowski reissue patent and were employed in the earliest devices implanted in patients. Biphasic pulses are disclosed in U.S. Pat. No. 4,953,551, issued to Mehra et al. Damped sinusoidal pulses are disclosed in U.S. Pat. No. 4,834,100, issued to Charms.

In spite of the gains in efficiency provided by the developments disclosed in the patents discussed above, efforts are presently underway to further reduce the size of current implantable defibrillator pulse generators to further simplify implant and enhance patient comfort. As the devices become smaller, it is anticipated that the surface areas of the defibrillator housings may become small enough to interfere ability of the housing to function efficiently as the subcutaneous defibrillation electrode.

SUMMARY OF THE INVENTION

It is an object of the invention to provide an implantable cardioverter with adequate subcutaneous electrode surface area and spatial distribution for efficient use in cardioversion, while reducing the volume of the rigid structure of the housing of the cardioverter, to enhance patient comfort at the implant site.

This object of the invention is accomplished by means of a large surface area flexible electrode bearing pad extending peripherally to and electrically connected to a conductive, rigid pulse generator housing. The peripherally extending electrode bearing pad may be conformed to the contours of the implant site pad further serves to stabilize the pulse generator within the subcutaneous tissue at the implant site and electrode assembly.

The preferred embodiment of the present invention provides a combined pulse generator and electrode assembly for use with at least one remote electrode, wherein the assembly comprises a hermetically sealed housing enclosing a defibrillator pulse generator and having a rigid housing with a conductive exterior surface that is electrically coupled to the pulse generator to function as an electrode in conjunction with an electrode pad formed of an insulating, flexible material attached to and extending outward from the housing periphery in a generally parallel relation with respect to the major surfaces of the pulse generator housing surface. The electrode pad preferably carries an electrode array supported by the electrode bearing pad and distributed over at least the major portion of at least one surface of the pad, and electrically connected to the conductive surface of the housing. In a preferred embodiment, the electrode array is distributed over both of the upper and lower surfaces of the electrode bearing pad from the pad periphery inward to the conductive housing surface.

In the expected use of the invention, one endocardial electrode is located in the heart, for example in the right ventricle and the combined pulse generator housing and electrode assembly is subcutaneously located in the left, pectoral region of the chest. The combined pulse generator and electrode assembly may be surgically stabilized in the pectoral region by sutures passed through the insulating portion of the electrode bearing pad.

BRIEF DESCRIPTION OF THE DRAWINGS

These and other advantages, objects and features of the invention will be further understood when reference is made to the following description, taken in conjunction with the accompanying drawings, in which.

The drawings are not necessarily to scale.

DETAILED DESCRIPTION OF THE PREFERRED EMBODIMENTS

Figure 1:
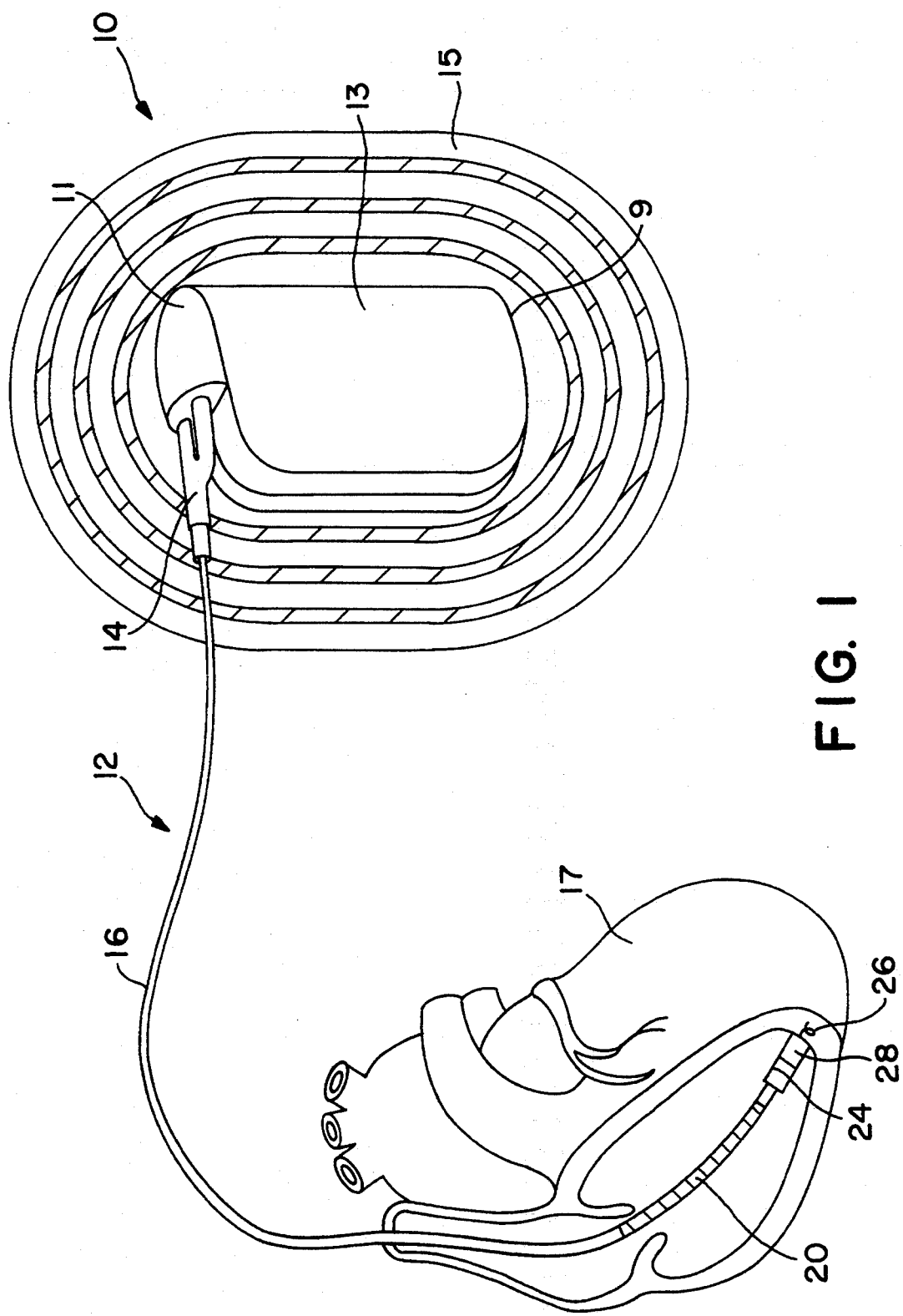
FIG. 1 illustrates the implantable defibrillator pulse generator and flexible electrode assembly, coupled to a defibrillation lead having an electrode located in the right ventricle of a human heart.

FIG. 1 illustrates the combined defibrillator pulse generator housing and flexible electrode assembly, according to the present invention, in conjunction with a transvenous lead 12 extending into the right ventricle of a heart 17. The lead 12 takes the form of the lead disclosed in the above cited Bardy, M.D. '400 and '838 patents, and includes an elongated insulating lead body 16, carrying three concentric coiled conductors, separated from one another by tubular insulating sheaths. Located adjacent the distal end of the lead 12 are a ring electrode 24, an extendable helix electrode 26, mounted to advance and retract within an insulating electrode head 28, and an elongated coil electrode 20. The defibrillation electrode 20 may be fabricated from platinum, platinum alloy or other materials known to be usable in implantable defibrillation electrodes. Electrodes 24 and 26 are employed for cardiac pacing and for sensing ventricular depolarizations.

Each of the electrodes 20, 24 and 26 is coupled to one of the coiled wire conductors within the lead body 16 in a manner well known in the art. At the proximal end of the lead is a bifurcated connector 14 which carries three electrical connectors (not shown), each coupled to one of the coiled wire conductors. The two connectors coupled by coiled wire conductors to the pace/sense electrode pair 24, 26 are arranged on a common connecter pin, and the other connector coupled by a further coiled wire conductor to the defibrillation electrode 20 forms the second connector pin of the bifurcated connector 14.

The bifurcated connector 14 is thus electrically connected to an implantable defibrillator pulse generator in a known manner. In the preferred embodiments of the invention described hereafter, the defibrillator pulse generator is a multi-programmable device that provides bradycardia and anti-tachycardia pacing, cardioversion and defibrillation, depending on the nature of the detected heart rhythm and programmed-in operating modes. A specific example of a pacing/cardioversion/defibrillation pulse generator, which may be used in conjunction with the illustrated lead system to deliver biphasic pulses, is disclosed in the above incorporated Mehra et al. '551 patent.

The combined implantable defibrillator pulse generator and electrode assembly 10 of FIG. 1 includes an active electrode formed of the entire exterior surface 13 of the metallic pulse generator housing 9 by attaching the housing 9 internally to a defibrillation circuit output terminal. Optionally, the major upper surface of the housing (the surface intended to face toward the exterior of the patient's body) may be coated with insulation, so that the exterior surface 13 is exposed on only the major lower surface of the housing (the surface intended to face toward the interior of the patient's body).

The defibrillator pulse generator housing 9 carries a connector block 11, into which the bifurcated connector 14 is inserted and mechanically and electrically coupled so that the other electrode 20 and the pace/sense electrodes 24 and 26 may be coupled to the circuitry within the housing 9.

In accordance with the invention, the subcutaneous electrode surface area is increased and distributed over a wider area by coupling it to an electrode array formed in and exposed on one or both surfaces of the flexible electrode bearing pad 15. Preferably, the flexible pad 15 is permanently bonded to housing 9 around its periphery. The active electrode is thereby formed as part or all of the pulse generator housing surface 13 and the electrode array formed in the flexible electrode pad 15, described hereafter. The flexible electrode bearing pad 15 is relatively flat and is fabricated of a flexible biopcompatible material such as silicone rubber or polyurethane.

Figure 2:
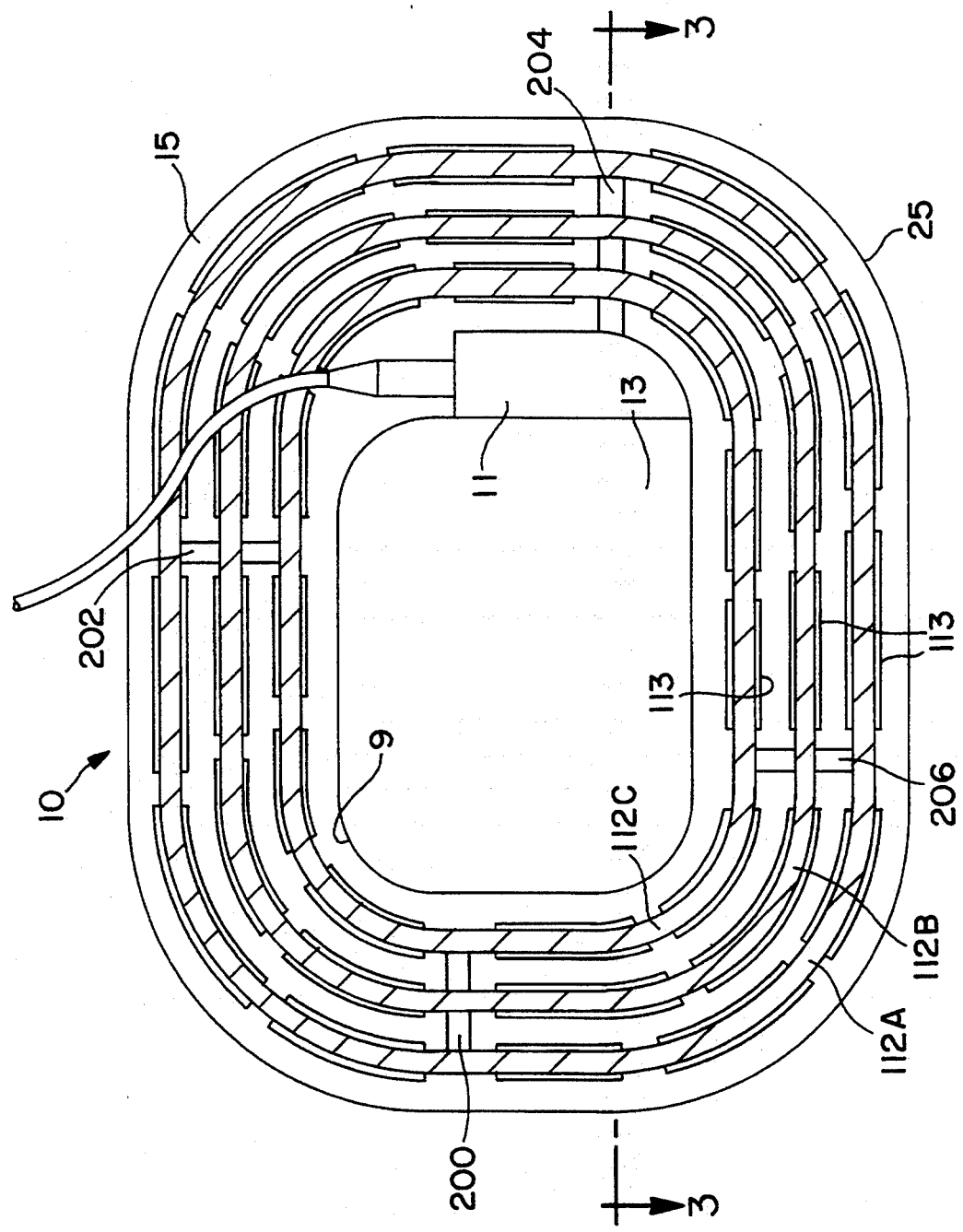
FIG. 2 is a top view of a combined pulse generator housing and flexible electrode assembly according to one embodiment of the present invention.

Turning to FIG. 2, one embodiment of the combined housing and electrode assembly 10 is depicted in greater detail. The flexible electrode bearing pad 15 is attached around the edge of the pulse generator housing 9. The electrode bearing pad 15 is formed in a shape that extends beyond the periphery of the defibrillator housing and terminates in a flexible pad periphery 25. The pad 15 may be formed in any shape dependent on or independent of the shape of the pulse generator housing.

The electrode bearing pad 15 has a plurality of space-wound coil electrodes 112A, 112B and 112C, which are spaced from one another and embedded within corresponding grooves molded in the major lower surface of the electrode pad 15. The electrode coils may be mounted in grooves in the manner described in the '374 patent, incorporated herein by reference, so that the coils are exposed only on the lower surface of the pad. Preferably, however, the grooves are cut away to form openings as illustrated at 113, so that the coils are exposed to both the major upper and lower surfaces of pad 15 along the majority of their length. As a further alternative to providing openings 13, the portion of the pad 15 extending peripheral to the outer coil 112A may instead be removed, providing exposure of outer coil 112A to both major surfaces of the pad 15. Electrode coils 112A, 112B and 112C are interconnected by means of conductive strips 200, 202, 204 and 208, which may be welded to the coils at their points of attachment. Strip 204 is coupled to the housing 9, internal to connector block 11.

Figure 3:
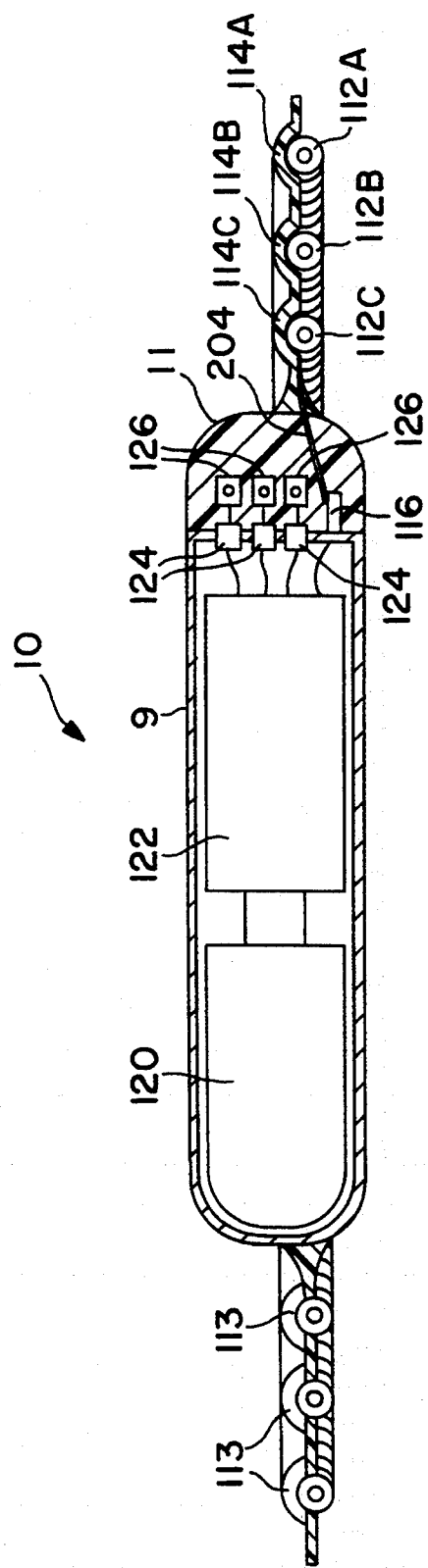
FIG. 3 is a sectional view through the pulse generator and electrode assembly illustrated in FIG. 2.

FIG. 3 illustrates a sectional view through the combined housing and pad 10. The electrode coils 112A, 112B and 112C are electrically connected together and to pin 116 extending from the wall of the pulse generator housing 9 by conductive strip 204. In this view, the electrode coils 112A, 112B and 112C are shown embedded within grooves 114A, 114B and 114C, respectively, molded into the electrode pad, shown cut away at openings 113. The subcutaneous electrode surface provided is thus distributed spatially across both major surfaces of the pad 15 between the pulse generator periphery and the pad periphery 25.

Although FIG. 3 is a cross section elevation of FIG. 2 along, the components depicted within the housing 10 and connector block 12 may not be in their true relation to the section line illustrated in FIG. 2 and are depicted to show their general relation and interconnection merely for purposes of completeness. No specific relation or interconnection of the components of the pulse generator within the pulse generator housing or the connector block 12 is necessary to the practice of the invention. Thus, the battery and high voltage capacitor package 120 is shown electrically connected to the electronic module 122. The input and output circuits of the electronic module, including one output of the cardioversion pulse generator included therein are coupled by feed-throughs 124 extending through the hermetic enclosure of the housing 10 and to terminal block components 126 in the connector block 11 in a manner known in the art. One cardioversion pulse generator output from circuitry 122 is coupled by means of a jumper wire to the housing 9. The bifurcated connector 14 of the lead 12 may be connected the terminal block components 126 within the connector block 11 in a manner known in the art.

The relative dimensions of the defibrillator pulse generator housing 9 in relation to the electrode bearing pad 15 may vary from those shown. As the pulse generator components become more miniaturized the distributed electrode surface area afforded by the electrode array of the electrode bearing pad 15 may correspondingly increase. The electrode surface area and distribution over the pad 15 may also vary from that shown in FIGS. 2 and 3.

While the invention as described above employs an electrode pad permanently mounted to the housing of the cardioverter/defibrillator, It is within the scope of the present invention to provide an electrode pad which may optionally be coupled to the housing prior to implant. One embodiment of such a device would employ an electrode bearing pad formed having a central opening corresponding to the periphery of the device housing. Interconnection of the electrode surfaces on the pad and the housing may be accomplished in this case by means of an additional lead connector coupled to the electrode surfaces on the pad, and insertable in the connector block carried by the housing or by means of direct connection to the exterior of the housing. The electrode pad in such an embodiment may also be mechanically attached to the housing by means of clips or other fasteners.

In each of the embodiments and variations thereon, it is to be understood that the pad periphery is intended to be thin and flexible so that it may be bent and conformed to the contours of the tissue at the implantation site. Moreover, attachment of the combined assembly to subcutaneous tissue may be facilitated by passing sutures through the periphery of the pad at one or more locations, and through adjacent tissue thereby avoiding rotation or migration of the assembly. Optionally, suture tabs may be formed as part of the electrode pad.

In conjunction with the above specification, I claim:

1. An implantable cardioverter, comprising:
a hermetically sealed housing having a conductive major surface enclosing a cardioversion pulse generator, said cardioversion pulse generator having an output coupled to said major conductive surface;
a flexible, generally planar electrode beaming pad having first and second major surfaces generally extending from and generally parallel to said major conductive surface, said electrode bearing pad being formed of a biocompatible, flexible material and having an inner periphery adjacent said housing and an outer periphery spaced therefrom;
an electrode array supported by said electrode bearing pad and having conductive electrode surfaces distributed over said electrode pad between said inner and outer peripheries of said pad and electrically coupled to said conductive major surface of said housing.

2. The apparatus of claim 1 wherein said electrode array further comprises a plurality of spaced electrode coils electrically connected in common.

3. The apparatus of claim 2 wherein said electrode pad is provided with grooves formed in said first major surface, in which said electrode coils are mounted.

4. The apparatus of claim 3 wherein said electrode pad is provided with openings therethrough, exposing said electrode coils to said first and second major surfaces of said pad.

5. The apparatus of claim 3 wherein an outermost one of said electrode coils is exposed to said first and second major surfaces of said pad.

6. The apparatus of claim 1 wherein said electrode array further comprises a plurality of spaced electrode surfaces electrically connected in common and distributed over said first major surface of said electrode pad between said inner and outer peripheries.

7. The apparatus of claim 1 wherein said electrode pad is fixedly mounted to said housing.

* * * * *